US006604115B1

(12) United States Patent
Gary, Jr. et al.

(10) Patent No.: US 6,604,115 B1
(45) Date of Patent: Aug. 5, 2003

(54) METHOD AND APPARATUS FOR STORING DATA

(75) Inventors: Wyndham Fairchild Gary, Jr., Whitefish Bay, WI (US); Richard G. Adcock, Sioux Falls, SD (US)

(73) Assignee: GE Marquette Medical Systems, Inc., Milwaukee, WI (US)

( * ) Notice: Subject to any disclaimer, the term of this patent is extended or adjusted under 35 U.S.C. 154(b) by 174 days.

(21) Appl. No.: 09/703,365

(22) Filed: Oct. 30, 2000

Related U.S. Application Data

(60) Provisional application No. 60/163,668, filed on Nov. 5, 1999.

(51) Int. Cl.$^7$ .............................................. G06F 17/30
(52) U.S. Cl. ................................. 707/104.1; 707/513
(58) Field of Search .................. 119/14.47; 600/508, 600/509, 510; 707/104.1, 1, 2, 4, 100, 101, 102

(56) References Cited

U.S. PATENT DOCUMENTS

| | | | |
|---|---|---|---|
| 5,020,540 A | 6/1991 | Chamoun | 600/509 |
| 5,555,403 A | 9/1996 | Cambot et al. | 707/4 |
| 5,732,708 A * | 3/1998 | Nau et al. | 600/510 |
| 5,966,692 A | 10/1999 | Langer et al. | 600/509 |
| 5,976,082 A | 10/1999 | Wong et al. | 119/14.47 |
| 6,004,276 A * | 12/1999 | Wright et al. | 600/508 |
| 6,247,008 B1 | 6/2001 | Cambot et al. | 707/104.1 |
| 6,260,021 B1 * | 7/2001 | Wong et al. | 705/1 |
| 6,270,457 B1 * | 8/2001 | Bardy | 600/300 |
| 6,336,903 B1 | 1/2002 | Bardy | 600/508 |
| 6,463,417 B1 * | 10/2002 | Schoenberg | 705/2 |

OTHER PUBLICATIONS

HP "HP Introduces TraceMaster ECG Management system on Microsoft Windows NT platform" Aug. 17, 1999.*

* cited by examiner

*Primary Examiner*—Diane D. Mizrahi
*Assistant Examiner*—Yicun Wu
(74) *Attorney, Agent, or Firm*—Foley & Lardner; Peter J. Vogel; Michael A. Della Penna

(57) ABSTRACT

A method and apparatus of storing and accessing data from a database is disclosed. The method and apparatus applies particularly to database systems used for cardiovascular information systems but may also be used in other database systems. The method and apparatus for storing and accessing data utilizes a markup language tag data structure to provide for simplified and expedited searching over conventional databases.

25 Claims, 3 Drawing Sheets

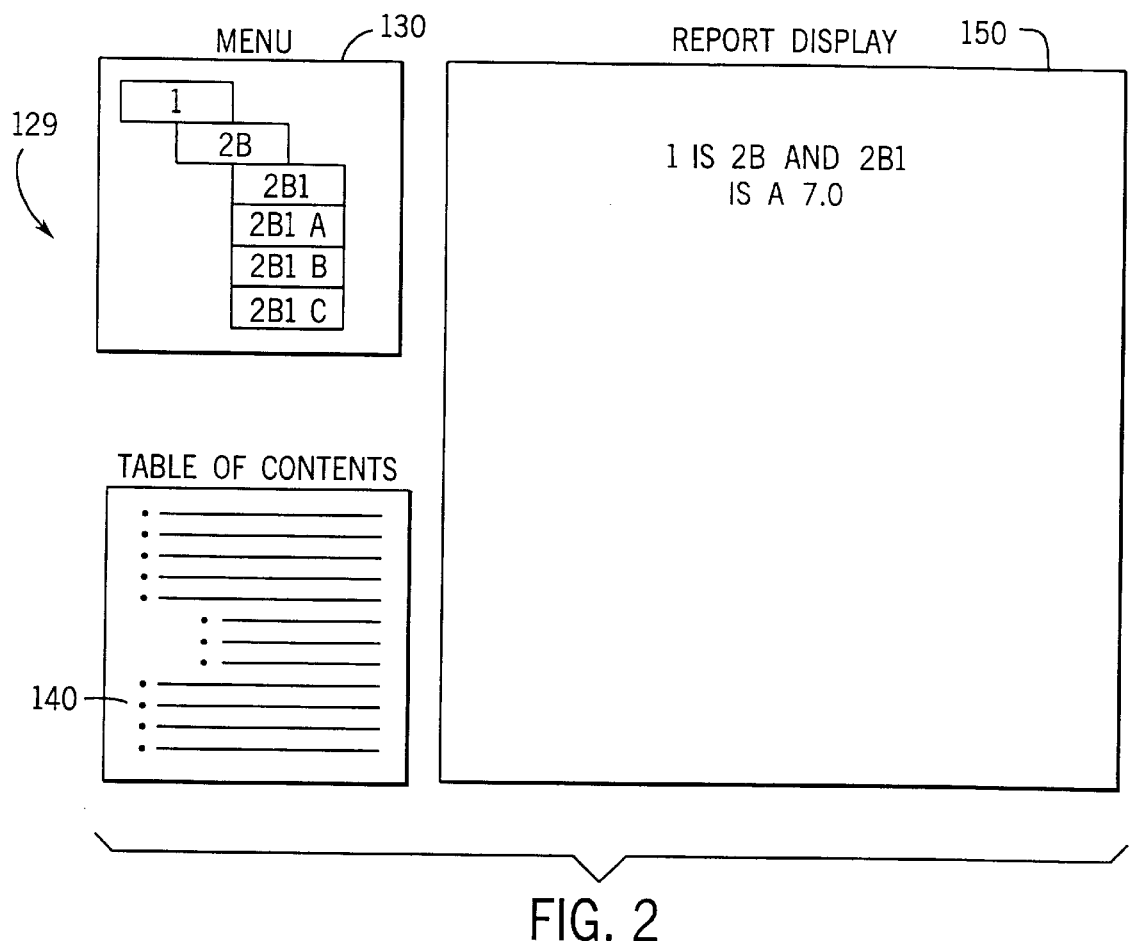
FIG. 2
FIG. 3
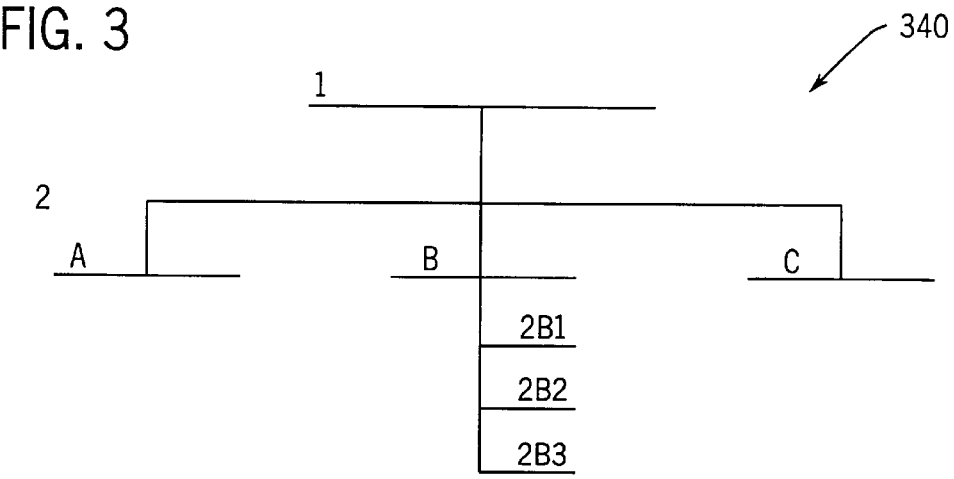

METHOD AND APPARATUS FOR STORING DATA

REFERENCE TO RELATED APPLICATIONS

This application claims the benefit of U.S. Provisional Application No. 60/163,668, filed Nov. 5, 1999.

FIELD OF THE INVENTION

The invention relates to information and database systems. More particularly, the invention relates to a method and apparatus of storing and accessing data from a database. More particularly still, the invention relates to a method and apparatus of storing and accessing data for a cardiovascular information system.

BACKGROUND OF THE INVENTION

In hospitals or other healthcare settings, it is frequently necessary to observe critical physiological conditions of a patient, including cardiovascular conditions. Cardiovascular condition data is obtained from sensors applied to a patient, or by imaging and sensing devices. Further, cardiovascular data may be data reported by a cardiologist based on review of a patient or a patient's monitor or image data. Hospitals or healthcare centers often have hundreds or even thousands of sensor and metering devices and hundreds or even thousands of cardiac patients that require monitoring periodically over a lifetime. This data may potentially be stored in a database for archival functions and later retrieval. However, searching of databases of this type are often difficult and require the programming of complex queries in order to locate the desired data. Furthermore, databases in general also require complex searching techniques in order to locate a desired data set or desired data quantity.

There is a need for a method and apparatus of storing and accessing data in a database that provides simplified searching and querying. Further, there is a need and desire for a method and apparatus for searching and querying a cardiovascular database.

SUMMARY OF THE INVENTION

An exemplary embodiment of the invention relates to a method of storing information in a cardiovascular database. The method includes storing a view data structure configured for structured cardiovascular patient data. The method also includes storing a tag configured to identify cardiovascular patient data element types. Further, the method includes storing a data element associated with a tag, the data element related to cardiovascular patient data associated with the view data structure.

Another exemplary embodiment of the invention relates to a method of accessing information in a medical database. The method includes querying a medical database for a specified data element meeting a specified condition. The method also includes retrieving a stored view data structure. Further, the method includes processing a plurality of records according to the view, the records including a plurality of tags and associated data elements. Further still, the method includes searching the plurality of records for a specified tag and testing a data element to determine whether the data element meets the specified condition.

Another embodiment of the invention further relates to an apparatus for storing and accessing information across a medical information system network. The apparatus includes a computer including a storage medium, a processor, and a memory. The apparatus also includes a program stored in the memory and running on the processor configured to access the storage medium according to a stored view data structure. The medical records on the storage medium are stored with a series of tags and data values and associated with a stored view and the program is configured to transform records from a transactional framework to an analytical framework.

Yet another exemplary embodiment of the invention relates to a method of storing information in a database. The method includes storing a view data structure configured for structured data. The method also includes storing a tag configured to identify data element types and storing data elements associated with the tag, the data elements related to data associated with the view data structure.

Still yet another exemplary embodiment of the invention relates to a method of accessing information in a database. The method includes querying a database for a specified item meeting a specified condition. The method also includes retrieving a stored view data structure and processing a plurality of records according to the view, the records including a plurality of tags and associated items. The method further includes searching the plurality of records for a specified tag and testing an item to determine whether the item meets the specified condition.

Yet still another exemplary embodiment of the invention relates to an apparatus for storing and accessing information. The apparatus includes a computer including a storage medium, a processor, and a memory. The apparatus also includes a program stored in the memory and running on the processor configured to access the storage medium according to a stored view data structure. The records on the storage medium are stored with a series of tags and data values and associated with a stored view. The program is configured to transform records from a transactional framework to an analytical framework.

BRIEF DESCRIPTION OF THE DRAWINGS

The invention will become more fully understood from the following detailed description, taken in conjunction with the accompanying drawings, wherein like reference numerals refer to like parts, in which:

FIG. 2 is a block diagram of a relational database display;

FIG. 3 is an exemplary diagram of a hierarchical tree database structure; and

DESCRIPTION OF EXEMPLARY EMBODIMENTS

Figure 1:
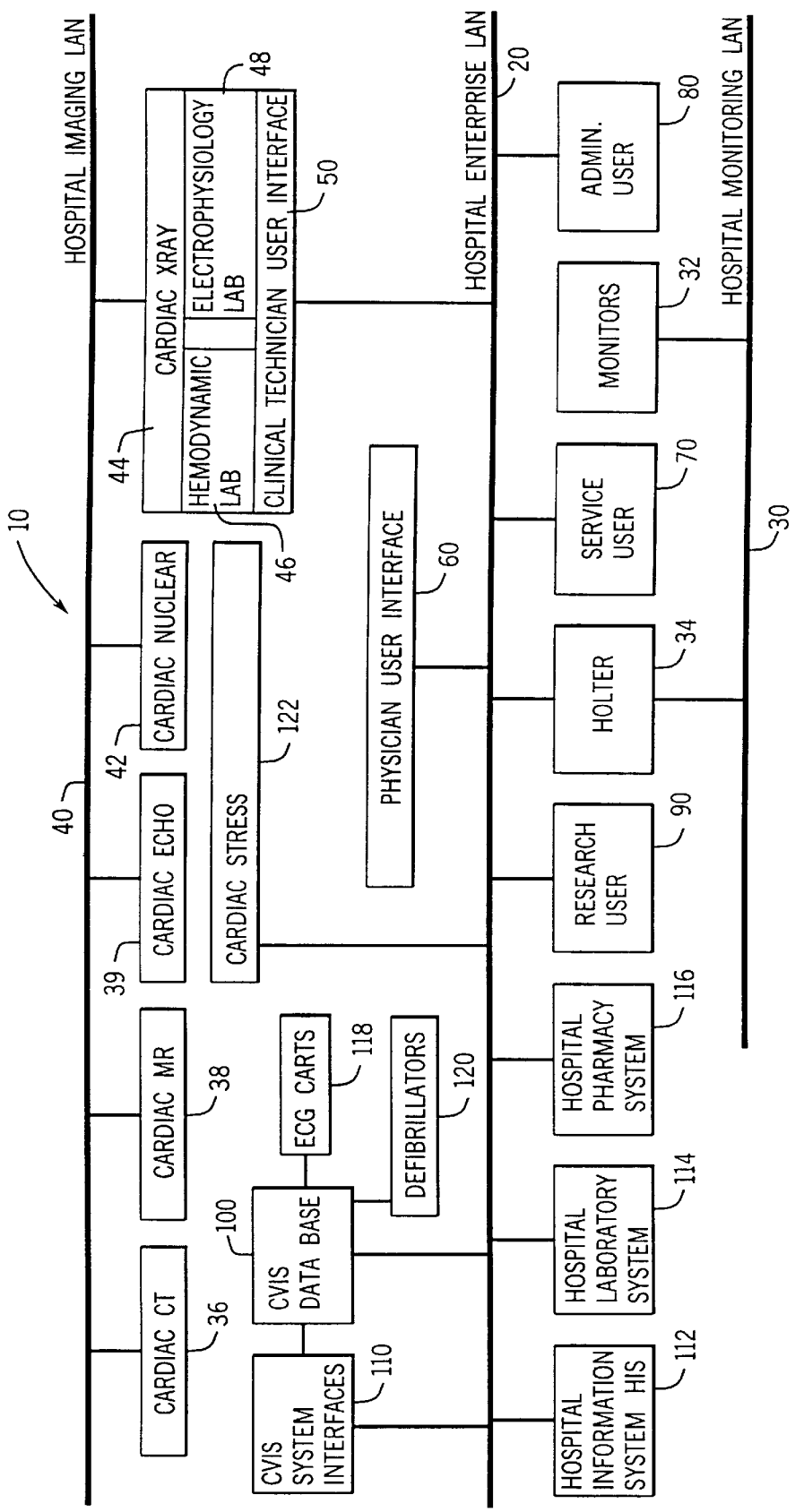
FIG. 1 is a block diagram of an exemplary embodiment of a cardiovascular information system.

Referring to FIG. 1, a block diagram of a cardiovascular information system (CVIS) 10 is shown. CVIS 10 includes a hospital enterprise network 20 which may be an intrahospital communications network or external communications network that is in communication with a plurality of other hospitals, service providers, equipment vendors, or other personnel (including, but not limited to, off-site doctors or healthcare technicians) or entities requiring information available from or provided by a hospital. CVIS 10 also includes a hospital monitoring network 30. Hospital monitoring network 30 may be, in An exemplary embodiment, an interhospital network such as the GE Marquette Unity Network® available from GE Marquette Medical, Inc., Milwaukee, Wis., or any other of a variety of mission critical networks utilizing any of a variety of applicable communication protocols. Further, hospital monitoring network 40 is a communications network that may be an ethernet network supporting transmission control protocol/internet protocol (TCP/IP) standards or any other applicable communication protocols.

In an exemplary embodiment, hospital monitoring network 30 may be used to share clinical information between different parts of a healthcare facility, such as, but not limited to cardiology, patient monitoring, hospital information, and laboratory equipment. Further, in an exemplary embodiment, hospital monitoring network 30 may be built using industry-standard equipment, including, but not limited to IEEE 802.3 (ethernet) cabling. A plurality of electronic devices, such as, but not limited to patient monitors 32 and holters 34 may be in communication with hospital monitoring network 30. Further, hospital monitoring network 30 may be coupled to any number of other electronic devices.

In an exemplary embodiment, CVIS 10 further includes a hospital imaging network 40 for communicating imaging information received from imaging devices such as cardiac imaging devices that include, but are not limited to, a cardiac computed tomography (CT) 36, a cardiac magnetic resonance (MR) 38, a cardiac ultrasound (or echo) 39, a cardiac nuclear imaging device 42, or a cardiac X-ray device 44. Each of these imaging devices is configured to provide imaging of the cardiovascular system of patients that can be stored and reviewed by physicians, clinical technicians, administrators, service users or researchers at a later time. Further, hospital imaging network 40 may be in communication with hospital enterprise network 20 through any of a plurality of communications connections.

Laboratory information, such as, but not limited to, hemodynamics lab 46 and electrophysiology lab 48 may be in communication with the hospital imaging network 40 and/or the hospital enterprise network 20.

A plurality of user interfaces are coupled to hospital enterprise network 20 including, but not limited to, a clinical technician user interface 50, a physician user interface 60, a service user interface 70, an administrator user interface 80 and a research user interface 90.

Clinical technician user interface 50 uses CVIS 10 to enter procedure and patient data. Entry of this data may, in an exemplary embodiment, be organized around current daily tasks performed for procedures. Many cardiac procedures may require data entry during the procedure which details the paths or actions taken, the timing of events during the procedure, etc. A clinical technician using clinical technician user interface 50 may optionally enter information before beginning the procedure which may be used during the procedure and further the clinical technician may optionally enter information after the procedure to aid in determining the procedure efficacy.

In an exemplary embodiment, physician user interface 60 may utilize a single screen which contains all test and report data that is pertinent for viewing during evaluation of a cardiology patient and which may be used to produce a final report. The data on the single screen for the physician user interface may include but is not limited to image data, hemodynamics data, waveform data, and patient demographic data. Further, other combinations of data may be utilized and/or viewed on the single screen.

In an exemplary embodiment, service user interface 70 is an interface to CVIS 10 that allows reviewing of error logs and system status information to diagnose and correct system faults and failures. A service user, which includes third party or off-site service users or customer based service users, will be able to review error logs from any and/or all devices or software applications of CVIS 10. Access to service user interface 70 may be under password control. In an exemplary embodiment, a service technician utilizing service user interface 70 will be locked out from reviewing any patient specific data. Further, a service technician utilizing service user interface 70 will be able to install network licensed feature additions. Further still, in an exemplary embodiment, a service technician utilizing service user interface 70 will be able to remotely access all service tools and data on site as well as remotely through any of a variety of communications networks including, but not limited to, the world wide web.

In an exemplary embodiment, administrator user interface 80 is configured to collect, display, and report department data for best practices in clinical and financial outcome analysis. Using a single application, the administrative user may be able to access, analyze, and generate departmental data for financial and clinical outcomes. The data generated may utilize conventional off the shelf software which may allow connectivity to third party outcome software packages. In an exemplary embodiment, the data accessed by an administrative user may have the ability to be exported to other data warehouses in standard formats, including, but not limited to, XML, HTML, or DICOM.

Further still, in an exemplary embodiment, research user interface 90 will enable a research user to interface to CVIS 10 by facilitating searching CVIS database 100 for research purposes. A researcher will be able to access database 100 utilizing a plurality of methods and database access schema relevant to the relationship of the database tables and database elements.

Each of these user interfaces is in communication with and provides viewing of information from CVIS database 100 through a search or query system. Further, a CVIS system interface 110 is coupled to hospital enterprise network 20. CVIS system interface 110 provides interfaces to any of hospital information system 112, hospital laboratory system 114 or hospital pharmacy system 116. The function of CVIS system interfaces 110 is to convert the data from systems 112, 114, and 116 into the format used by CVIS database 100. Further, CVIS database 100 may be coupled directly to electrocardiogram (ECG) carts 118 and/or defibrillators 120. In a preferred embodiment, cardiac stress testing information that is accumulated during cardiac stress tests 122 may be communicated to CVIS database 100 through hospital enterprise network 20.

CVIS database 100 interfaces hospital enterprise network 20, hospital monitoring network 30, and hospital imaging network 40 and provides a database of all the cardiovascular information for any given patient. The CVIS database 100 itself may include two databases, a first database may connect directly to ECG carts 118 and defibrillators 120 while a second database connects directly to all of the other hospital and lab information systems. In a preferred embodiment, CVIS database 100 includes information from traditional cardiovascular monitors such as ECG carts, defibrillators, and holters. In a preferred embodiment, CVIS database 100 also stores information from echo imaging, nuclear imaging, laboratory interfaces, X-ray interfacing, CT imaging and MR imaging all on one system. Further, in a preferred embodiment, CVIS database 100 provides for better reporting and customization through a structured reporting tool that allows cardiologists to rapidly create reports in a queriable format, including, but not limited to ODBC formats. Database 100 may maintain a log of all transactions and an error log of failed transactions. Further, database 100 may be configured to recover transactions which failed.

In an exemplary embodiment, CVIS 10 may be software which runs on server and client devices. The servers may be standard Microsoft® or Unix compatible hardware devices with options for raid disk configurations and archive media. It is desirable for such servers to include uninterrupted power supplies. An exemplary server configuration may be 100 megabyte Ethernet, 128 megabyte ram, 9 gigabyte disk, CD drive, 1024 by 768 video interface with keyboard and mouse. The clients may be, in an exemplary embodiment, Microsoft® compatible hardware devices. An exemplary client configuration may be 100 megabyte Ethernet, 64 megabyte ram, 4 gigabyte disk, CD drive, 1024 by 1280 by 70 hertz video interface with keyboard and mouse. CVIS 10 may be partitioned into server software and client software. The server software may be partitioned into database software (included in, for example, CVIS database 100), system interface software (included in, for example, CVIS system interfaces 110) device interface software, and server applications. The client software may be partitioned into structured reporting, user interface, and database manipulation applications.

Figure 4:
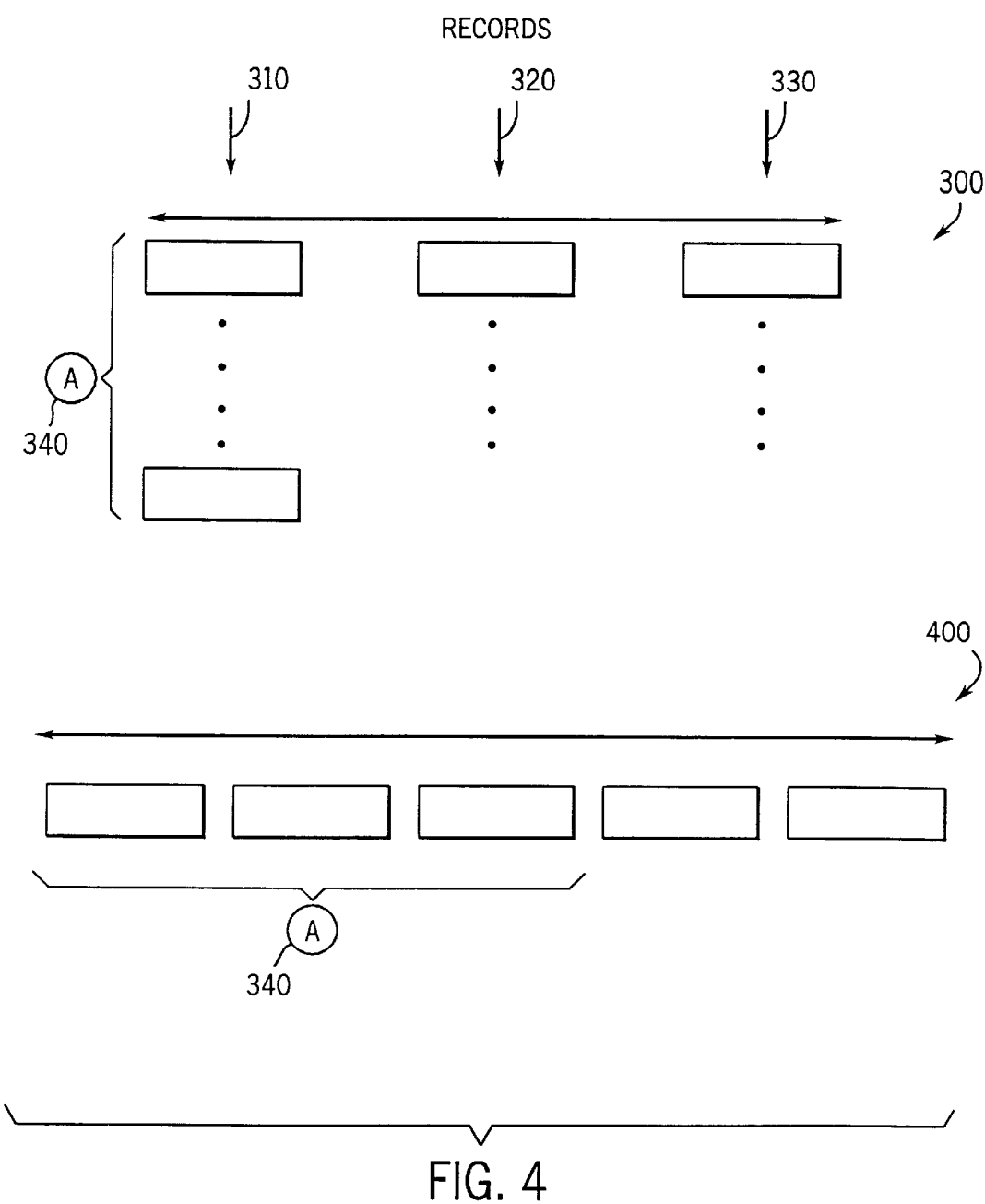
FIG. 4 is a diagram depicting a database transactional processing view and a database analytical processing view.

Further, CVIS database 100 may provide decision support for a physician that will aid the cardiologist in making treatment decisions. Decision support may include software logic configured to provide physician-like analysis of cardiac information stored in the database. In a preferred embodiment, CVIS 100 is a relational database that allows for storing relational deep data as depicted in FIG. 4, in which the records are stored in an on-line (or possibly an off-line) transactional processing configuration 300 in which the records may be viewed and stored as columns. Each record 310, 320 and 330 may correspond (for example) to a specific or a particular test or test result.

In a preferred embodiment, an interface 129 (FIG. 2) to the database includes three windows, a menu window 130, a table of contents window 140 and a display window or report window 150. The underlying database may be configured as a hierarchical tree 340 (as depicted in FIG. 3) that governs the menu selections 130 of FIG. 1. The database is configured such that the data is stored in an on-line transactional processing manner 300 and is accessed and searched in an on-line analytic processing manner 400.

In order to store information in the database, a user will be able to click through the menu 130 to create a sentence (or record), as shown in display 150. The report 150 may be stored as a text string similar to a markup language text string, in a preferred embodiment similar to XML. Each record may be stored as a marked up text string, for example, "<tag 1>value1</tag1><tag2>value2*b*</tag2><tag3>value2*b*1</tag3>". In a preferred embodiment, records may be accessed in on-line analytical processing view 400. On-line analytical processing view 400 allows the records to be stored as a series of strings, for example, the record labeled A 340 may be stored end to end (serially) with a plurality of other records in on-line analytical processing view 400. This allows a user to write a query that is more efficient than if one were to access records in on-line transactional processing view 300 where each record would need to be accessed individually and all elements of each record accordingly searched.

In operation, to convert from on-line transactional processing view 300 to on-line analytical processing view 400, database 100 takes the stored data in on-line transactional processing view 300, feeds each record through the associated view, stored in database 100, and provides end to end record strings that can be searched in a simplified and expedited manner.

As an example, a cardiologist in preparing a stress report may read in an analysis such as "lateral ST leads are abnormal at 3.2 millimeters of deviation or greater." Conventionally, this will be stored as a searchable text string in the database. Next time, however, when the cardiologist has a similar situation he may recite "the lateral ST are abnormal." Therefore, the order in which he recites the report, the terminology he uses, and the omission of certain terms makes it very difficult for the text string to be searched. In an exemplary embodiment, each single keyword, for example, lateral, ST deviation, and the measurement of it are all tagged. Because each word or measurement is tagged, the ability exists to database those pieces of information in a structured manner. Now, for example, the cardiologist has said that the ST in the lateral leads are abnormal at 3.2 millimeters of deviation ("<Type>ST deviation</Type><Locale>lateral</Locale><ST>3.2</ST>"). This data is tagged and stored. Later on researchers wish to conduct a drug study. They are looking for people with ST deviations of greater than 3.2 millimeters in the lateral leads because, for example, they are afraid that this drug will have an adverse effect on those patients. The doctor wants to search on the target population. First, the doctor may want to search all the patients that have an ST greater than 3 in the lateral leads. Therefore, he can search the on-line analytical processing view 400 simply looking for ST leads greater than 3.2 ("<ST> greater than 3.2 </ST>"). Because of the standardization used with the markup language tagging system, searching is not required through different types of records to find procedures that may be named something different. Further, because each sentence is parseable in that the structure is "<tag>value</tag><tag>value</tag><tag>value</tag>", the searching task is simplified and expedited.

Each record stored in the database is stored with a view. Each of these views is stored in the database separately, as separate records or in a separate table. Each view is used for different types of records, or records which change structure at a later date. To recreate a complete record, each stored record is put through the associated view to get a complete record, such as reported in display 150. When a report is stored, a view identifier is stored along with it.

Storing data using a tagged markup language allows on the fly customization. If it is necessary to modify reports, it is not necessary to modify the way the data is stored. All that needs to be done to accommodate a new report is to store a new view which can be applied to either new records or old records using the new view.

While the exemplary embodiments refer to a method and apparatus for storing and accessing data in a database for cardiovascular medicine, the subject matter may also be applied to databases in general even those not having to do with medical databases. Further, those who have skill in the art will recognized that the present invention is applicable with many different hardware and software configurations and organizations.

While the detailed drawings, specific examples, and particular formulations given describe exemplary embodiments, they serve the purpose of illustration only. For example, the data structures defined may differ and are not limited to the precise details and conditions disclosed.

Furthermore, other substitutions, modifications, changes, and omissions may be made in the design, operating conditions, and arrangement of the exemplary embodiments without departing from the spirit of the invention as expressed in the appended claims.

What is claimed is:

1. A method of accessing textual cardiovascular examination information in a cardiovascular database, comprising:
   transcribing a first cardiovascular patient record by,
      selecting a first data type in a menu window including;
         inputting a first data element associated with the first data type;
         tagging the first data element with a data type identifier;
         providing in the menu window, a plurality of second data type choices based on the first data type selected;
         selecting a second data type from the plurality of second data type choices;
         inputting a second data element associated with the second data type;
         tagging the second data element with a data type identifier; and
         storing a first view associated with the first cardiovascular patient record;
   retrieving a second stored view;
   converting the first cardiovascular patient record into the second view with a plurality of other stored cardiovascular patient records, thereby producing a string of cardiovascular patient records; and
   searching the string of records for a data element that meets a specified condition.

2. The method of claim 1 comprising:
   storing an alternative view data structure.

3. A method of accessing information in a medical database, comprising:
   querying a the medical database for a specified data element meeting a specified condition;
   transcribing a first cardiovascular patient record by,
      selecting a first data type in a menu window including;
      inputting a first data element associated with the first data type;
      tagging the first data element with a data type identifier;
      providing in the menu window, a plurality of second data type choices based on the first data type selected;
      selecting a second data type from the plurality of second data type choices;
      inputting a second data element associated with the second data type;
      tagging the second data element with a data type identifier; and
      storing a first view associated with the first cardiovascular patient record;
   retrieving a second stored view;
   converting the first cardiovascular patient record into the second view with a plurality of other stored cardiovascular patient records, thereby producing a string of records;
   searching the string of records for the data element that meets the specified condition; and
   testing the data element to determine whether the data element meets the specified condition.

4. The method of claim 3 wherein the database is a patient record database.

5. The method of claim 3 wherein the database is a cardiovascular database.

6. The method of claim 3 wherein the first view is a transactional view and the second view is an analytical view.

7. The method of claim 3 further comprising:
   defining a hierarchical structure of tags.

8. An apparatus for storing and accessing information across a medical information system network, comprising:
   a computer including a storage medium, a processor, and a memory; and
   a program stored in the memory and running on the processor configured to access the storage medium according to the steps of,
      transcribing a first cardiovascular patient record by,
         selecting a first data type in a menu window including;
            inputting a first data element associated with the first data type;
            tagging the first data element with a data type identifier;
            providing in the menu window, a plurality of second data type choices based on the first data type selected;
            selecting a second data type from the plurality of second data type choices;
            inputting a second data element associated with the second data type;
            tagging the second data element with a data type identifier; and
            storing a first view associated with the first cardiovascular patient record;
      retrieving a second stored view;
      converting the first cardiovascular patient record into the second view with a plurality of other stored cardiovascular patient records, thereby producing a string of records; and
      searching the string of records for a data element that meets a specified condition.

9. The apparatus of claim 8 further comprising a communications network coupled to the computer.

10. The apparatus of claim 9 further comprising a plurality of medical devices coupled to the communications network.

11. The apparatus of claim 10 further comprising a plurality of workstations coupled to the communications network.

12. The apparatus of claim 11 wherein at least one of the plurality of workstations is configured to run a research user interface.

13. A method of accessing information in a database, comprising:
   retrieving a plurality of patient records which are stored in columns of a patient records database, each column corresponding to a separate patient record;
   storing the plurality of patient records end to end in a single string of records; and
   searching the string of records for a data element that meets a specified condition.

14. The method of claim 13 comprising:
   storing an alternative view data structure.

15. The method of claim 13 wherein the information is cardiovascular information.

16. A method of accessing information in a database, comprising:
   transcribing a first cardiovascular patient record by,
      selecting a first data type in a menu window including;

inputting a first data element associated with the first data type;

tagging the first data element with a data type identifier;

providing in the menu window, a plurality of second data type choices based on the first data type selected;

selecting a second data type from the plurality of second data type choices;

inputting a second data element associated with the second data type;

tagging the second data element with a data type identifier;

storing a first view associated with the first cardiovascular patient record;

displaying in a report window the first cardiovascular patient record formatted according to the first view; and retrieving a second stored view;

converting the first cardiovascular patient record into the second view with a plurality of other stored cardiovascular patient records, thereby producing a string of records;

searching the string of records for a data element that meets a specified condition;

searching the plurality of records for a specified tag; and testing an item to determine whether the item meets the specified condition.

17. The method of claim 16 wherein the database is a medical database.

18. The method of claim 16 wherein the database is a cardiovascular database.

19. The method of claim 16 wherein the processing step includes transforming records from a transactional framework to an analytical framework.

20. The method of claim 16 further comprising:

defining a hierarchical structure of tags.

21. An apparatus for storing and accessing information, comprising:

a computer including a storage medium, a processor, and a memory; and a program stored in the memory and running on the processor configured to access the storage medium according to the steps of, transcribing a first cardiovascular patient record by,
selecting a first data type in a menu window including;

inputting a first data element associated with the first data type;

tagging the first data element with a data type identifier;

providing in the menu window, a plurality of second data type choices based on the first data type selected;

selecting a second data type from the plurality of second data type choices;

inputting a second data element associated with the second data type;

tagging the second data element with a data type identifier; and storing a first view associated with the first cardiovascular patient record;

retrieving a second stored view;

converting the first cardiovascular patient record into the second view with a plurality of other stored cardiovascular patient records, thereby producing a string of records; and searching the string of records for a data element that meets a specified condition, wherein the records on the storage medium are stored with a series of tags and data values and associated with a stored view and the program is configured to transform records from a transactional framework to an analytical framework.

22. The apparatus of claim 21 further comprising a communications network coupled to the computer.

23. The apparatus of claim 22 further comprising a plurality of medical devices coupled to the communications network.

24. The apparatus of claim 23 further comprising a plurality of workstations coupled to the communications network.

25. The apparatus of claim 24 wherein at least one of the plurality of workstations is configured to run a research user interface.

* * * * *

UNITED STATES PATENT AND TRADEMARK OFFICE
CERTIFICATE OF CORRECTION

PATENT NO. : 6,604,115 B1
DATED : August 5, 2003
INVENTOR(S) : Wyndham Fairchild Gary, Jr. and Richard G. Adcock It is certified that error appears in the above-identified patent and that said Letters Patent is hereby corrected as shown below:

<u>Column 7,</u>
Line 36, delete the word "a" after the word "querying."

Signed and Sealed this

Twenty-eighth Day of October, 2003

JAMES E. ROGAN
*Director of the United States Patent and Trademark Office*